United States Patent
Onouchi (10) Patent No.: US 11,160,517 B2
(45) Date of Patent: Nov. 2, 2021

(54) RADIATION IMAGING DEVICE (71) Applicant: Hitachi, Ltd., Tokyo (JP)

(72) Inventor: Masafumi Onouchi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 8 days.

(21) Appl. No.: 16/644,010

(22) PCT Filed: Aug. 27, 2018

(86) PCT No.: PCT/JP2018/031503
§ 371 (c)(1),
(2) Date: Mar. 3, 2020

(87) PCT Pub. No.: WO2019/142385
PCT Pub. Date: Jul. 25, 2019

(65) Prior Publication Data
US 2021/0000433 A1 Jan. 7, 2021

(30) Foreign Application Priority Data

Jan. 18, 2018 (JP) .............................. JP2018-006228

(51) Int. Cl.
*A61B 6/06* (2006.01)
*A61B 6/03* (2006.01)
*A61B 6/00* (2006.01)

(52) U.S. Cl.
CPC .................. *A61B 6/06* (2013.01); *A61B 6/03* (2013.01); *A61B 6/4241* (2013.01)

(58) Field of Classification Search
CPC ........... A61B 6/06; A61B 6/03; A61B 6/4241; G01T 7/00
See application file for complete search history.

(56) References Cited

U.S. PATENT DOCUMENTS

| 10,222,488 B2* | 3/2019 | Danielsson ............. G01T 1/243 |
| 2003/0128812 A1 | 7/2003 | Appleby et al. |
| 2008/0165922 A1 | 7/2008 | Yanoff et al. |
| 2008/0175347 A1* | 7/2008 | Tkaczyk ................... G01T 1/24 378/7 |

(Continued)

FOREIGN PATENT DOCUMENTS

| JP | 2003-307570 A | 10/2003 |
| JP | 2007-010559 A | 1/2007 |

(Continued)

OTHER PUBLICATIONS

International Search Report, dated Nov. 20, 2018, which issued during the prosecution of International Application No. PCT/JP2018/031503, which corresponds to the present application.

*Primary Examiner* — Marcus H Taningco
(74) *Attorney, Agent, or Firm* — Baker Botts L.L.P.

(57) ABSTRACT

It is possible to reduce the weight of an anti-scatter collimator and to improve uniformity of scattered radiation shielding rate. A radiation imaging device has a radiation source, a radiation detector that detects radiation emitted from a focus of the radiation source, and an anti-scatter collimator provided between the radiation source and the radiation detector. The anti-scatter collimator has a septum provided at a predetermined interval along a radiation incident direction on a boundary between pixels of the radiation detector. The upper end of a top septum corresponds with a radiation incident surface.

11 Claims, 11 Drawing Sheets (56) References Cited

U.S. PATENT DOCUMENTS

| | | | |
|---|---|---|---|
| 2016/0356730 A1 | 12/2016 | Handa | |
| 2019/0090827 A1* | 3/2019 | Wieczorek | G21K 1/025 |
| 2020/0234839 A1* | 7/2020 | Choquette | G21K 1/025 |

FOREIGN PATENT DOCUMENTS

| | | |
|---|---|---|
| JP | 2008-168125 A | 7/2008 |
| JP | 2009-276138 A | 11/2009 |
| JP | 2013-140121 A | 7/2013 |
| JP | 2015-166735 A | 9/2015 |
| JP | 2016-007424 A | 1/2016 |

* cited by examiner

RADIATION IMAGING DEVICE

TECHNICAL FIELD

The present invention relates to a radiation imaging device in which a photon counting type detector is mounted and relates to an anti-scatter collimator for removal of scattered radiation.

BACKGROUND ART

In recent years, development of a photon counting CT (Computed Tomography) device, in which a detector using a photon counting method (photon counting type detector) is mounted, is advanced in various facilities. The photon counting type detector is, different from a charge integration type detector employed in conventional CT devices, capable of individually counting radiation photons incident on a semiconductor layer as a detection device. The photon counting type detector is capable of measuring energy of each of radiation photons. Accordingly, in the photon counting type CT device, in comparison with the conventional CT devices, it is possible to obtain more information.

In the radiation imaging device represented by the CT device, to suppress incident of scattered radiation occurred on a subject or the like on the detector, an anti-scatter collimator which is a slit or a grid made of a heavy metal such as tungsten, molybdenum, tantalum, or the like, is provided in front of the detector. In the photon counting CT device which measures energy of each of the radiation photons, since it is necessary to further improve a scattered radiation shielding rate, the anti-scatter collimator tends to be taller. When the height of the anti-scatter collimator made of a heavy metal is increased, the weight of the anti-scatter collimator is increased. The increase in the weight of the anti-scatter collimator disturbs high-speed rotation of the CT device.

In PTL 1, an anti-scatter collimator in which a frame is laminated is disclosed. The frame has a groove in which a wire of molybdenum or the like is extended in a tensioned state. The pitch between the wires is 2 or larger integer multiple of the pixel size of the detector.

The position of the wire is shifted between adjacent frames in the laminating direction. Although there is no definite description about weight reduction of the anti-scatter collimator in PTL 1, as the wires as septa of the anti-scatter collimator are thinned in the structure, the weight of the anti-scatter collimator is reduced.

CITATION LIST

Patent Literature

PTL 1: Japanese Patent Application Laid-Open No. 2007-10559

SUMMARY OF INVENTION

Technical Problem

However, in the anti-scatter collimator disclosed in PTL 1, in a surface which the radioactive ray enters, the height of the septum of the anti-scatter collimator is not even. The scattered radiation shielding rate differs in accordance with position within a detection surface of the detector, and is nonuniform. When the scattered radiation shielding rate is nonuniform, the measurement accuracy of radiation photon energy is lowered, and a misdiagnosis might be caused with the obtained medical image.

Accordingly, the present invention has an object to provide a radiation imaging device in which the weight of the anti-scatter collimator is reduced and the uniformity of the scattered radiation shielding rate is improved.

Solution to Problem

To attain the above object, the characteristic feature of the present invention is to provide a radiation imaging device including: a radiation source; a radiation detector that detects radiation emitted from a focus of the radiation source; and an anti-scatter collimator provided between the radiation source and the radiation detector. The anti-scatter collimator has a septum provided at a predetermined interval along a radiation incident direction on a boundary between pixels of the radiation detector, and the upper end of a top septum corresponds with the radiation incident surface.

Advantageous Effects of Invention

According to the present invention, it is possible to provide a radiation imaging device in which the weight of the anti-scatter collimator is reduced and the uniformity of the scattered radiation shielding rate is improved.

DESCRIPTION OF EMBODIMENTS

Hereinbelow, embodiments of the present invention will be described with reference to the drawings. A radiation imaging device according to the present invention is applied to a device having a radiation source and a photon counting type detector. In the following description, the radioactive ray is an X-ray, and the radiation imaging device is an X-ray CT device.

First Embodiment

Figure 1:
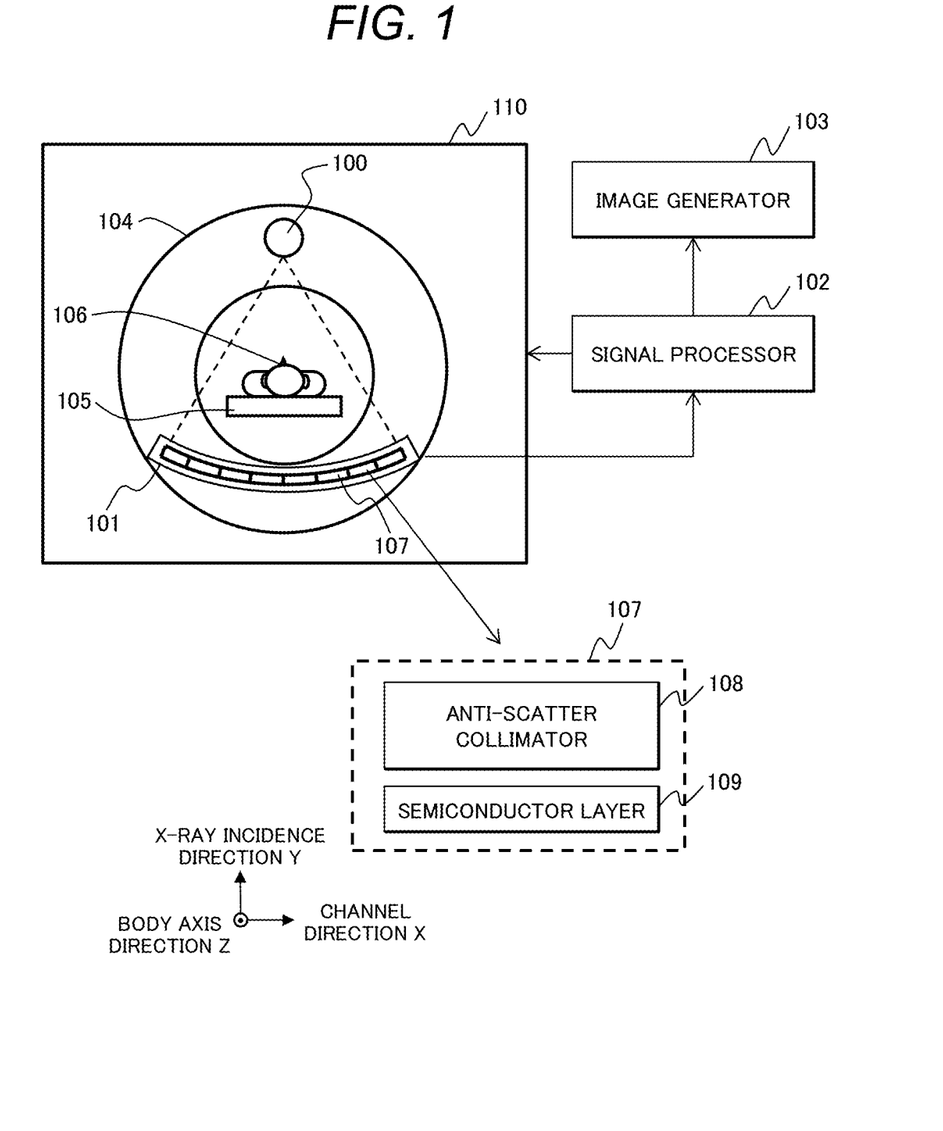
FIG. 1 is a diagram showing the entire configuration of an X-ray CT device to which the present invention is applied.

As shown in FIG. 1, the X-ray CT device according to the present embodiment has an X-ray source 100 to perform irradiation with an X-ray, an X-ray detector 101 with plural two-dimensionally arrayed detection devices to detect the X-ray, a signal processor 102 to perform processing such as correction on a detection signal from the detection device and to control the device, and an image generator 103 to generate an image of a subject 106 by using the corrected signal. The X-ray source 100 and the X-ray detector 101 are fixed to a rotary table 104 in positions opposite to each other, and configured so as to relatively rotate around the subject 106 laid down on a bed 105. Note that a part including the X-ray source 100, the X-ray detector 101, and the rotary table 104 is also referred to as a scanner 110.

The X-ray detector 101 is configured with detection element modules 107 arrayed in an arc shape about the X-ray source 100. The X-ray incident direction is a longitudinal direction of the paper (Y), the channel direction is a horizontal direction of the paper (X), and the body axis direction is a vertical direction of the paper (Z). The detection element module 107 is a photon counting type detector. The detection element module 107 has a semiconductor layer 109 to output an electric charge corresponding to incident X-ray photons, an anti-scatter collimator 108, and a photon counting circuit (unshown). The anti-scatter collimator 108 reduces cross-talk between pixels formed in the semiconductor layer and scattered radiation caused by the subject 106 and the like. The photon counting circuit counts the electric charge outputted from the semiconductor layer 109, and outputs a count signal. The semiconductor layer 109 is, as in the case of conventional semiconductor layers, a semiconductor layer of cadmium zinc telluride (CZT), cadmium telluride (CdTe) or the like. The anti-scatter collimator and a more particular configuration of an attachment part of the anti-scatter collimator will be described later.

The imaging operation of the X-ray CT device having the above configuration is the same as the imaging operation of the conventional X-ray CT device. In a state where the X-ray source 100 and the X-ray detector 101 are provided oppositely to each other, the X-ray is irradiated from the X-ray source 100 and the X-ray transmitted through the subject 106 is detected with the X-ray detector 101 while the X-ray source 100 and the X-ray detector 101 rotate around the subject 106. The signal processor 102 performs processing such as correction on the count signal outputted from the photon counting circuit of the X-ray detector 101 as needed. Then, the image generator 103 generates a tomographic image (CT image) of the subject.

Figure 2:
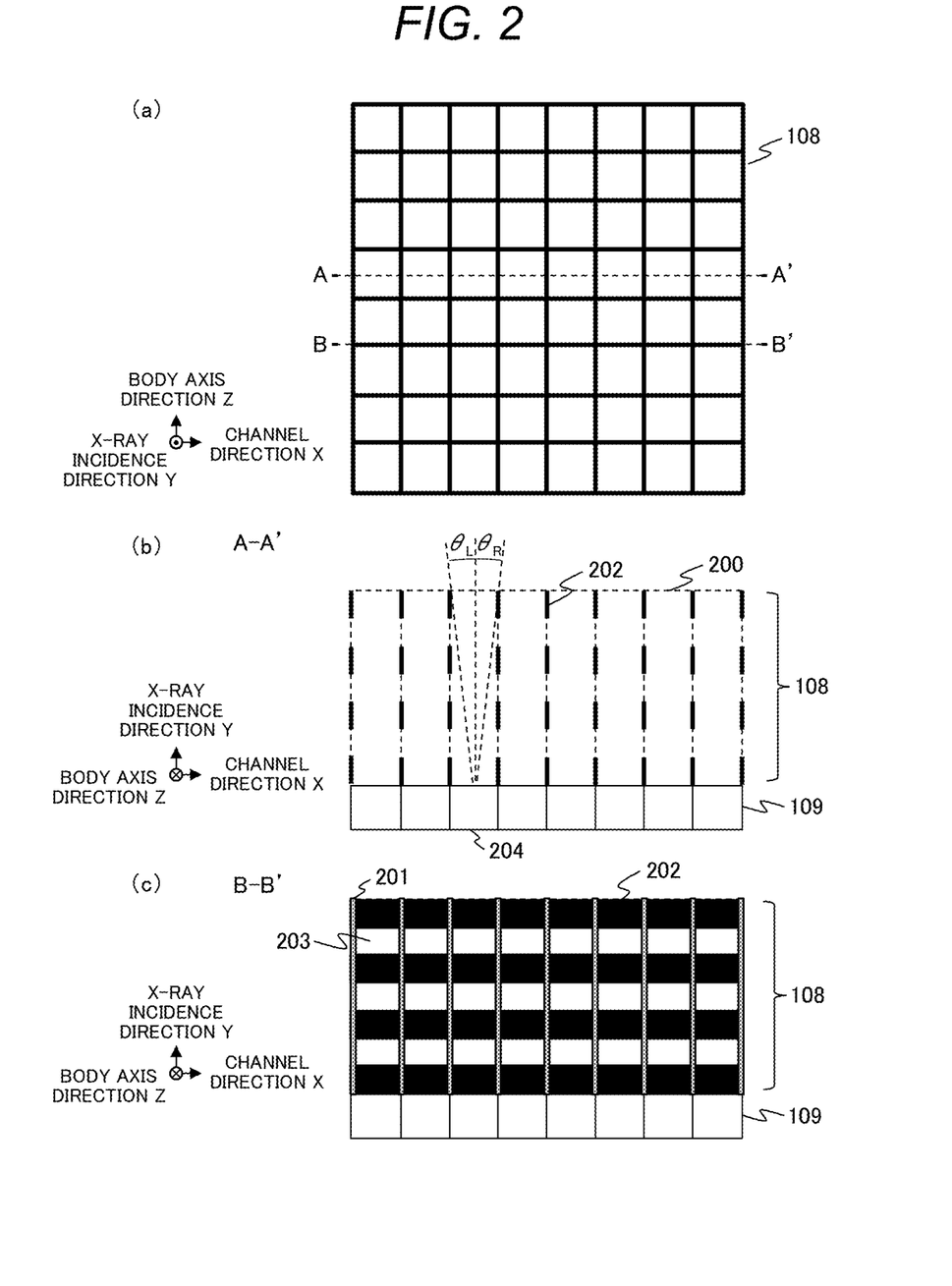
FIG. 2 is a diagram showing an example of the shape of an anti-scatter collimator according to a first embodiment.

The anti-scatter collimator 108 according to the present embodiment will be described by using FIG. 2. FIG. 2(a) is a plane view of the anti-scatter collimator 108, FIG. 2(b) is an A-A' cross-sectional view, and FIG. 2(c) is a B-B' cross-sectional view. In FIG. 2(a), the X-ray incident direction (Y) is a vertical direction of the paper, the body axis direction (Z) is a longitudinal direction of the paper, and the channel direction (X) is a horizontal direction of the paper. Note that the body axis direction (Z) and the channel direction (X) are also referred to as pixel array directions of the semiconductor layer 109.

The anti-scatter collimator 108 has a pillar 201 and a septum 202. The pillar 201 is made of a heavy metal such as tungsten, molybdenum, tantalum or the like. The pillar 201 is provided along the X-ray incident direction immediately above the four corners of the pixel in the semiconductor layer 109, to support the septum 202. The septum 202 is made of a heavy metal such as tungsten, molybdenum, tantalum or the like. The septum 202 is provided at a predetermined interval along the X-ray incident direction on a boundary between pixels. That is, plural septa 202 are provided on the boundary between pixels, and a gap 203 exists between the septa 202. With the existence of the gap 203 between the septa 202, it is possible to reduce the weight of the anti-scatter collimator 108.

Further, a septum positioned at the top among the plural septa 202 provided along the X-ray incident direction, i.e., the septum closest to the X-ray source 100, is provided such that the upper end of the septum corresponds with an X-ray incident surface 200. Since the upper end of the top septum corresponds with the X-ray incident surface 200, the optic angles from the center of the pixel 204 to the opening of the anti-scatter collimator 108 are symmetrical, i.e., $\theta_L = \theta_R$ holds. It is possible to improve the uniformity of the scattered radiation shielding rate.

Figure 3:
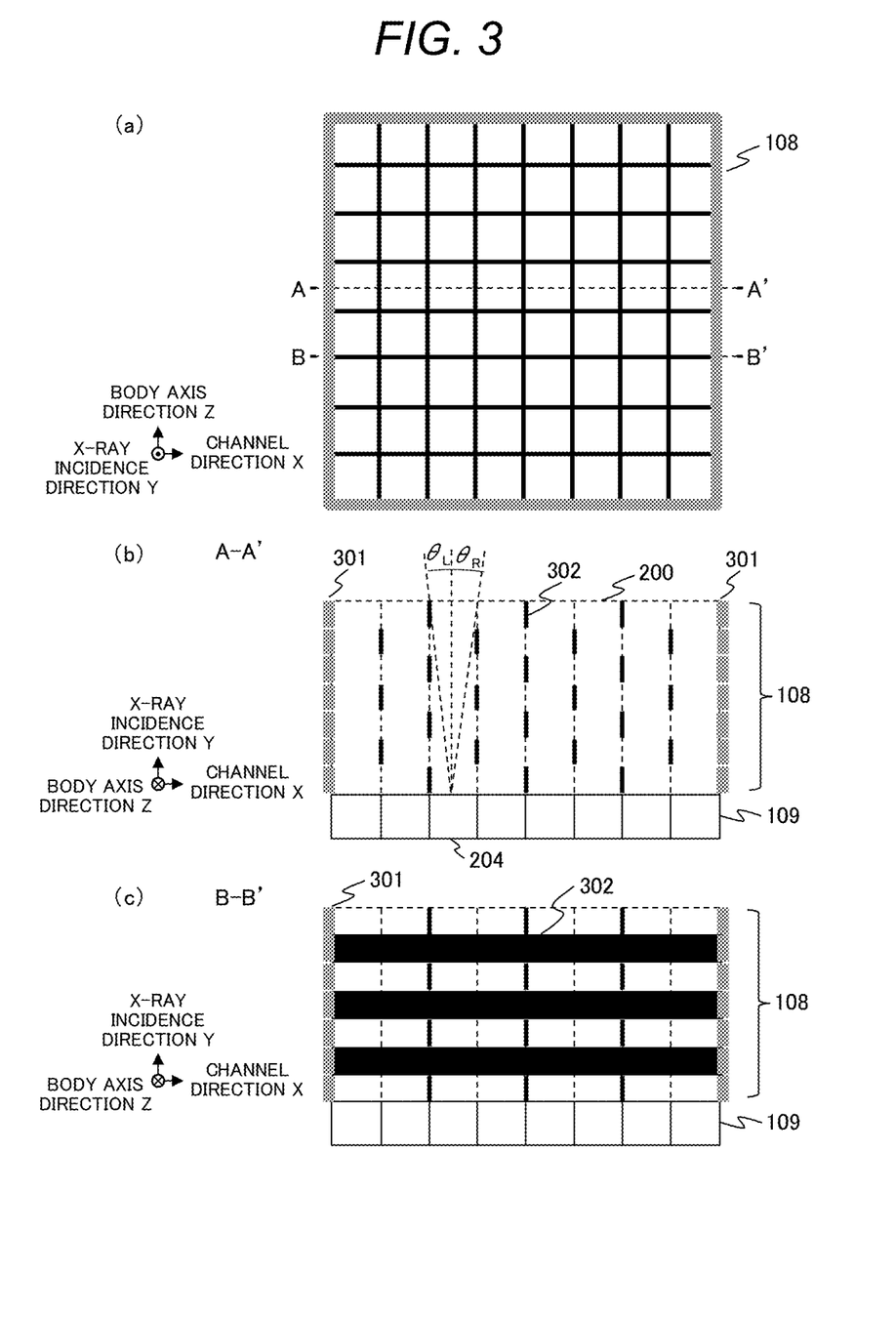
FIG. 3 is a diagram showing the shape of the anti-scatter collimator as a comparative example.

FIG. 3 shows the anti-scatter collimator 108 having a conventional structure as a comparative example. As in the case of FIG. 2, FIG. 3(a) is a plane view of the anti-scatter collimator 108, FIG. 3(b) is an A-A' cross-sectional view, and FIG. 3(C) is a B-B' cross-sectional view.

In the anti-scatter collimator 108 in FIG. 3, a frame 301, having a groove in which a wire 302 of molybdenum or the like is extended in a tensioned state, is laminated. The pitch between the wires 302 is 2 or a larger integer multiple of the pixel size of the detector. The position of the wire 302 is shifted between the frames 301 adjacent in the laminating direction. Since the wire 302 is provided at a predetermined interval in the X-ray incident direction, the weight of the anti-scatter collimator 108 is reduced. However, the X-ray incident surface 200 has a position in which the wire 302 exists and a position in which the wire 302 does not exist, the optic angles from the center of the pixel 204 to the opening of the anti-scatter collimator 108 are asymmetrical, i.e., $\theta_L < \theta_R$ holds. Whether the scattered radiation is eliminated or not depends on incident angle. As a result, the scattered radiation shielding rate is nonuniform in the conventional structure. In the present embodiment, the upper end of the top septum is made to correspond with the X-ray incident surface 200, to improve the uniformity of the scattered radiation shielding rate.

Figure 4:
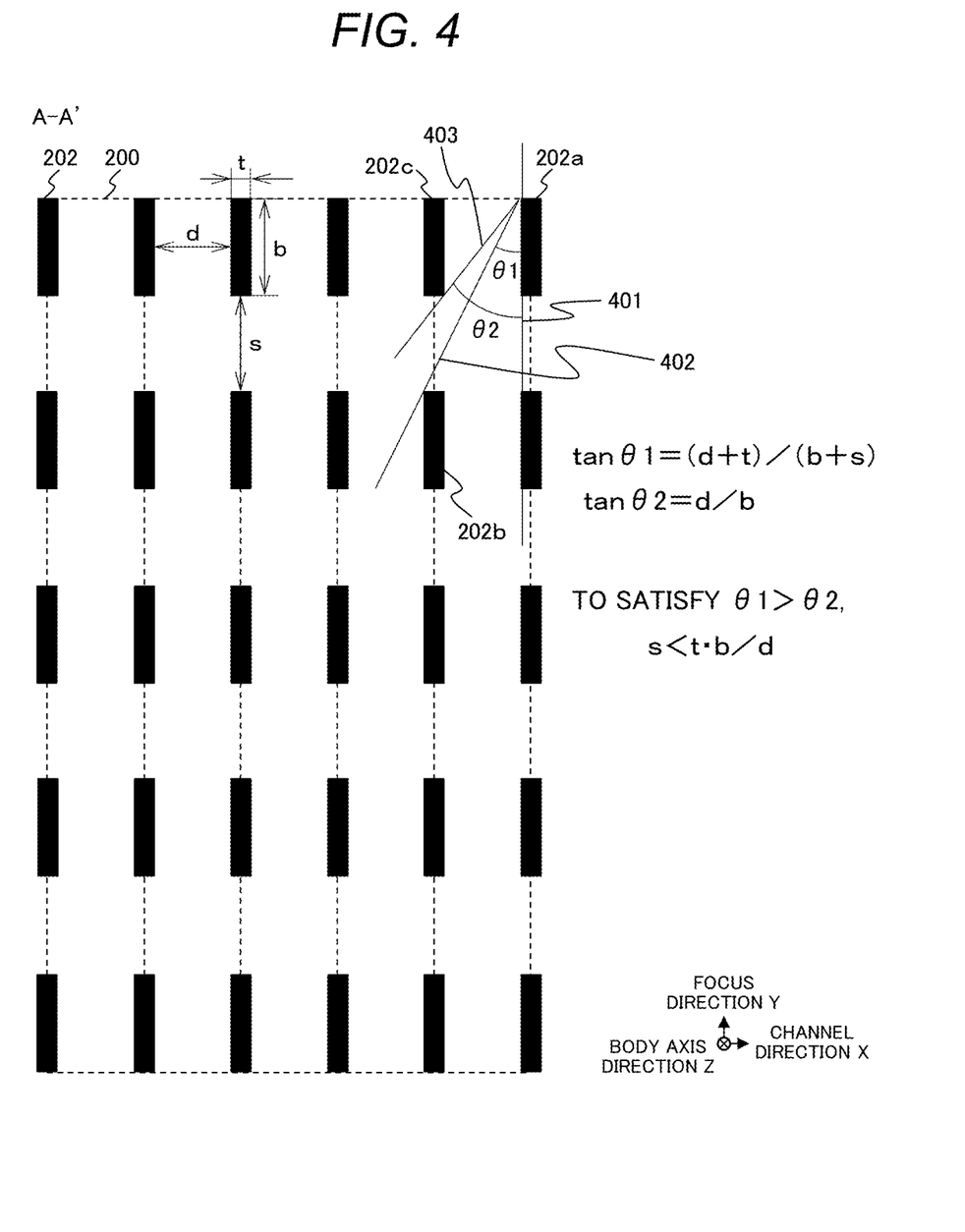
FIG. 4 is a diagram showing an arrangement example of a septum 202 according to the first embodiment.

Next, the arrangement of the septum 202 will be described by using FIG. 4 which is an enlarged view of FIG. 2(b). In FIG. 4, the septum 202 is provided in the channel direction (X) and in the X-ray incident direction (Y), respectively at an equal pitch. Note that the thickness of the septum 202 in the channel direction (X) is t, the height in the X-ray incident direction (Y) is b, the interval between the septa 202 in the channel direction (X) is d, and the interval in the X-ray incident direction (Y) is s. An angle θ1, formed between a route 402 connecting the vertex at the upper end of the top septum 202a with the vertex at the upper end of an adjacent septum 202b in a row below the top septum 202a, and a vertical line 401, is represented with an (Expression 1).

$$\tan\theta 1 = (d+t)/(b+s) \qquad \text{(Expression 1)}$$

Further, an angle θ2 formed between a route 403 connecting the vertex at the upper end of the top septum 202a with the vertex at the lower end of a septum 202c adjacent to the top septum 202a, and the vertical line 401, is represented with an (Expression 2).

$$\tan\theta 2 = d/b \qquad \text{(Expression 2)}$$

Note that so long as θ1>θ2 holds, it is possible to prevent passage of scattered radiation between the septum 202b and the septum 202c. Accordingly, the (Expression 1) and the (Expression 2) lead to an (Expression 3).

$$s < t \cdot b/d \qquad \text{(Expression 3)}$$

In the configuration of the detection element module 107, it is not preferable to change the thickness t of the septum 202 and the interval d in the channel direction (X). Accordingly, the septum 202 is provided such that the height b of the septum 202 in the X-ray incident direction (Y) and the interval s between the septa 202 satisfy the (Expression 3).

With the above-described arrangement of the septum 202, it is possible to reduce the weight of the anti-scatter collimator 108 and to improve the uniformity of the scattered radiation shielding rate.

Second Embodiment

In the first embodiment, the arrangement of the septum 202 at an equal pitch has been described. When the arrangement of the septum 202 does not satisfy the (Expression 3) though the septum 202 is arranged at an equal pitch, scattered radiation may be transmitted between the septa 202. In the present embodiment, to prevent transmission of scattered radiation, the septum 202 is provided such that the pitch in the X-ray incident direction (Y) is changed in the middle. Note that the upper end of the top septum is made to correspond with the X-ray incident surface 200 as in the case of the first embodiment.

Figure 5:
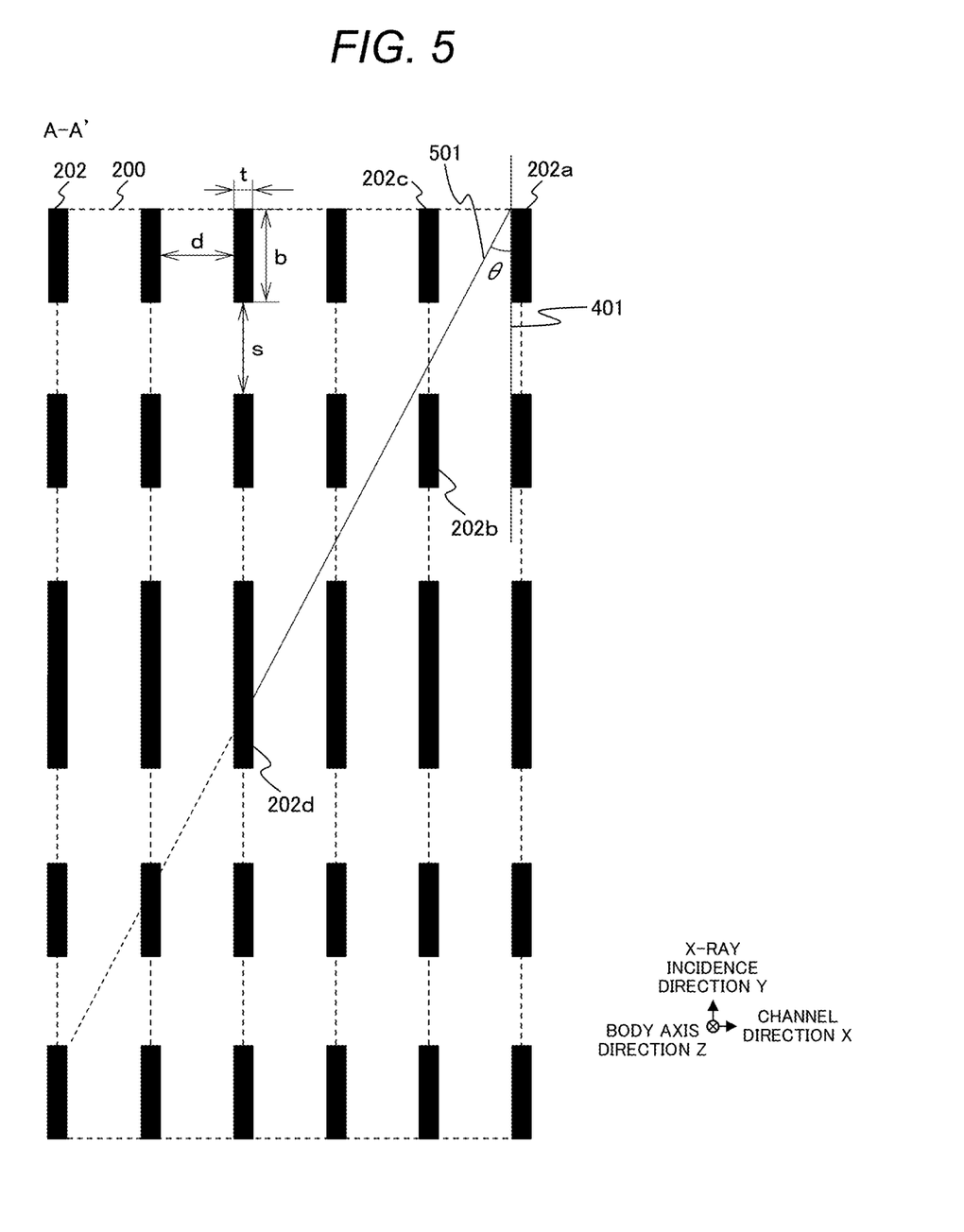
FIG. 5 is a diagram showing an arrangement example of the septum 202 according to a second embodiment.

The arrangement of the septum 202 in the present embodiment will be described by using FIG. 5. In FIG. 5, the septum 202 is provided at an equal pitch in the channel direction (X), and b=s and d>t hold. The arrangement does not satisfy the (Expression 3). Further, in the X-ray incident direction (Y), the septum is provided such that it is shifted by a half pitch in an intermediate position of the anti-scatter collimator 108.

By changing the pitch in the intermediate position of the anti-scatter collimator 108, a route 501 transmitted between the septum 202b and the septum 202c in the upper half of the anti-scatter collimator 108 is shielded with the septum 202d in the lower half of the anti-scatter collimator 108. That is, by providing the septum 202 as shown in FIG. 5, even when b=s and d>t hold and the arrangement does not satisfy the (Expression 3), it is possible to shield scattered radiation incident on the anti-scatter collimator 108 at an arbitrary angle θ. Further, as b=s holds, it is possible to further reduce the weight of the anti-scatter collimator 108 in comparison with the first embodiment. Further, since the tall septum 202 is provided in the intermediate position of the anti-scatter collimator 108, it is possible to enhance the rigidity with respect to the centrifugal force caused by rotation of the rotary table 104.

Note that in the present embodiment, the anti-scatter collimator 108 is divided into two in the X-ray incident direction (Y), and the septum 202 is provided such that the position of the septum is shifted by a half pitch in the intermediate position of the anti-scatter collimator 108. The shift of the pitch is not limited to this arrangement. When the anti-scatter collimator 108 is divided into three in the X-ray incident direction (Y), the septum 202 may be provided such that the position of the septum is shifted by ⅓ pitch in the position where the anti-scatter collimator 108 is divided. Further, as a generalized arrangement, when the anti-scatter collimator 108 is divided into N, the septum 202 may be provided such that the position of the septum is shifted by 1/N pitch in the respective dividing positions. Note that N is an integer equal to or larger than 2.

Third Embodiment

In the first embodiment and the second embodiment, it has been described that the interval s between the septa 202 in the X-ray incident direction (Y) is equal. The interval between the septa 202 is not limited to this example. In the present embodiment, the septum 202 is provided such that the interval s is changed in accordance with position in the X-ray incident direction (Y). Note that the upper end of the top septum is made to correspond with the X-ray incident surface 200 as in the case of the first embodiment.

Figure 6:
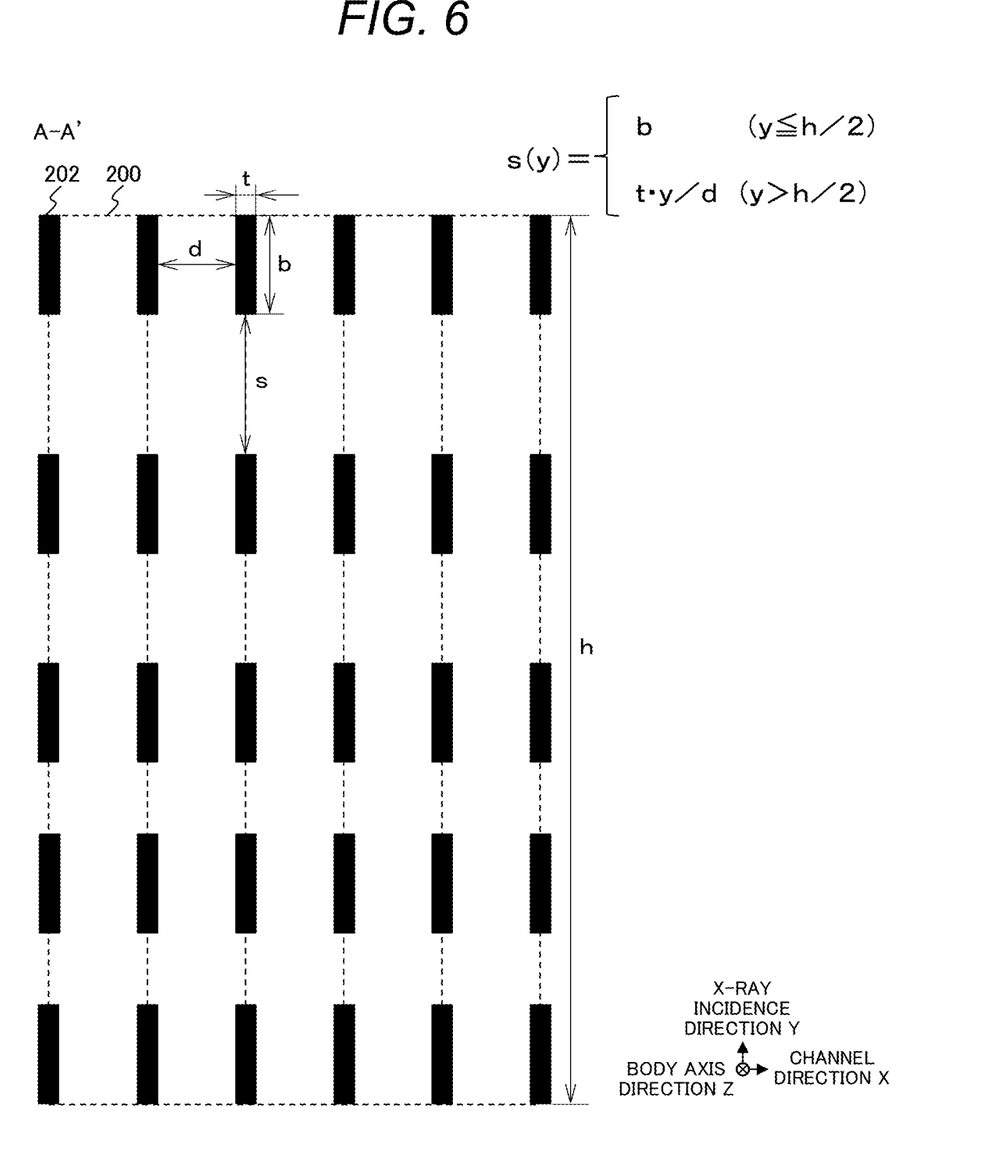
FIG. 6 is a diagram showing an arrangement example of the septum 202 according to a third embodiment.

The arrangement of the septum 202 in the present embodiment will be described by using FIG. 6. In FIG. 6, the septum 202 is provided at an equal pitch in the channel direction (X). In the X-ray incident direction (Y), the septum 202 is provided at an equal interval in the lower half of the anti-scatter collimator 108, and in the upper half of the anti-scatter collimator 108, the septum 202 is provided such that the interval s is increased in accordance with position rise in the X-ray incident direction (Y). That is, the interval s is represented, as a function s(y) in position y in the X-ray incident direction (Y), with e.g. an (Expression 4). Note that as the bottom position of the anti-scatter collimator 108, y=0 holds.

$$s(y)=b(y\leq h/2), t\cdot y/d(y>h/2) \quad \text{(Expression 4)}$$

Note that h is the height of the anti-scatter collimator 108. Further, s(y) may be an (Expression 5).

$$s(y)=b(y\leq b\cdot d/t), t\cdot y/d(y>b\cdot d/t) \quad \text{(Expression 5)}$$

The septum 202 is provided such that the interval s is the widest, i.e., the anti-scatter collimator 108 can be the lightest, by using e.g. the (Expression 4) or the (Expression 5) in accordance with values of b, d, t, and h.

By providing the septum 202 so as to satisfy the (Expression 4) or the (Expression 5), the scattered radiation is shielded, and the center of gravity of the anti-scatter collimator 108 is lowered. When the interval s between the septa 202 is equal, the center of gravity of the anti-scatter collimator 108 in the X-ray incident direction (Y) is in the intermediate position. In this case, the rigidity of the anti-scatter collimator 108 upon rotation of the rotary table 104 may be lowered. In the present embodiment, in the upper half of the anti-scatter collimator 108, the septum is provided such that the interval s is increased in accordance with position rise in the X-ray incident direction (Y). Accordingly, the center of gravity of the anti-scatter collimator 108 is lowered. It is possible to improve the rigidity of the anti-scatter collimator 108 upon rotation of the rotary table 104.

Fourth Embodiment

In the first embodiment, it has been described that the shape of the gap 203 between the septa 202 is a rectangle. When the shape of the gap 203 is a rectangle, the septum 202 protrudes in the horizontal direction. However, this shape is not appropriate to 3D printer molding. In this case, the lower surface of the septum 202 is lost, and the dimension accuracy is deteriorated. The deterioration of dimension accuracy in the lower surface of the septum 202 causes reduction of the scattered radiation shielding rate. In the present embodiment, the anti-scatter collimator 108 having a shape appropriate to 3D printer molding will be described. Note that the upper end of the top septum is made to correspond with the X-ray incident surface 200 as in the case of the first embodiment.

The anti-scatter collimator 108 according to the present embodiment will be described by using FIG. 7.

Figure 7:
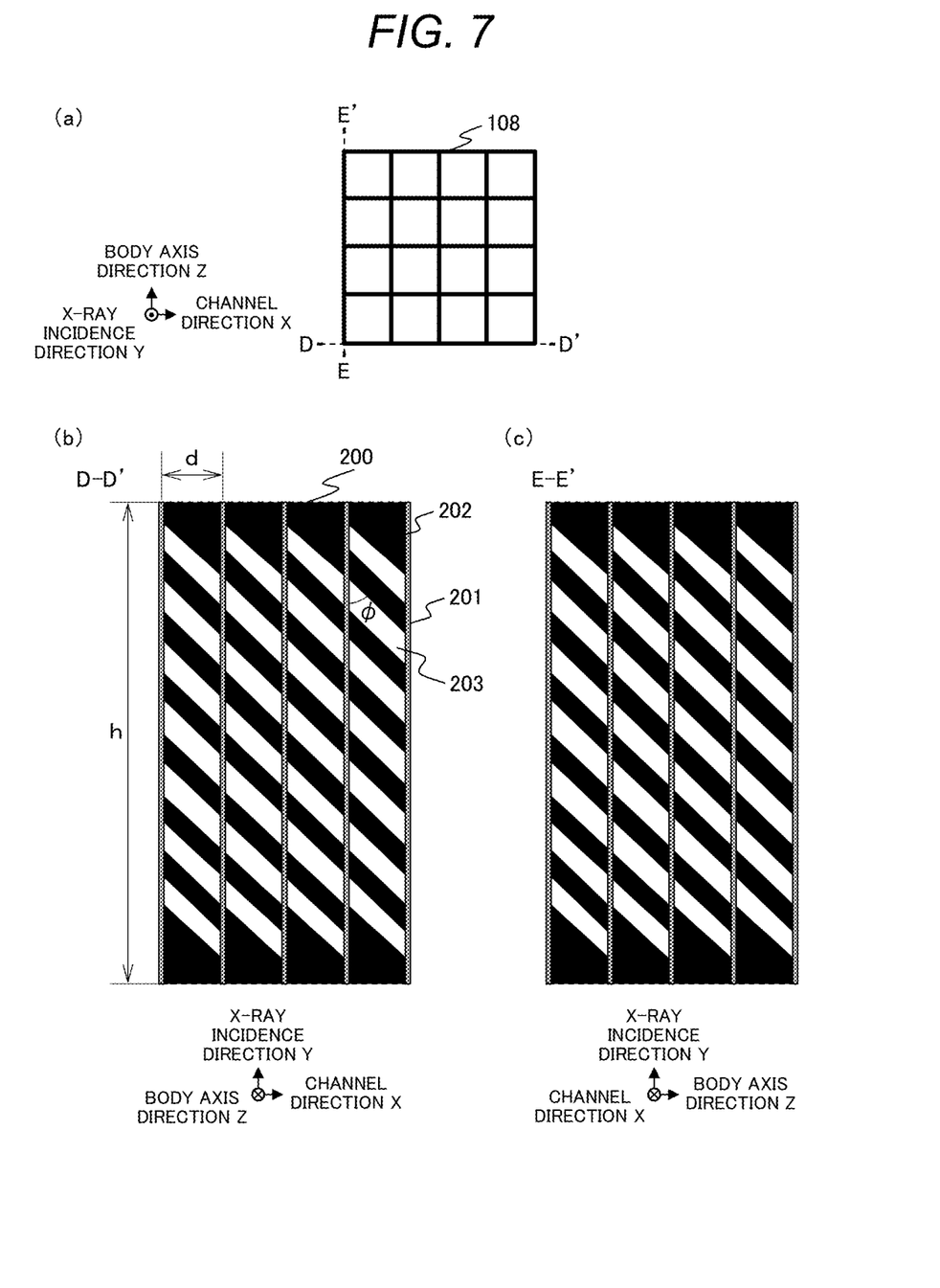
FIG. 7 is a diagram showing an example of the shape of the anti-scatter collimator according to a fourth embodiment.

FIG. 7(a) is a plane view of the anti-scatter collimator 108, FIG. 7(b) is a D-D' cross-sectional view, and FIG. 7(c) is an E-E' cross-sectional view. The anti-scatter collimator 108 according to the present embodiment is different from the first embodiment in that the shape of the gap 203 is a parallelogram. As the shape of the gap 203 is a parallelogram, the septum 202 protrudes in a direction at a predetermined angle φ from the horizontal direction. Even when the anti-scatter collimator 108 is molded with a 3D printer, it is possible to satisfy necessary dimension accuracy without damaging the lower surface of the septum 202.

Further, in the present embodiment, the septum 202 is provided at an equal pitch in the X-ray incident direction (Y), and the gap 203 has the same shape between adjacent pixels. This arrangement facilitates post-production inspection. Note that in the septum 202, the cross-sectional shape of the top and the bottom parts is different from the cross-sectional shape of other parts. The cross-sectional shape of the top and the bottom parts is a trapezoid, and the shape of the other parts is a parallelogram.

Figure 8:
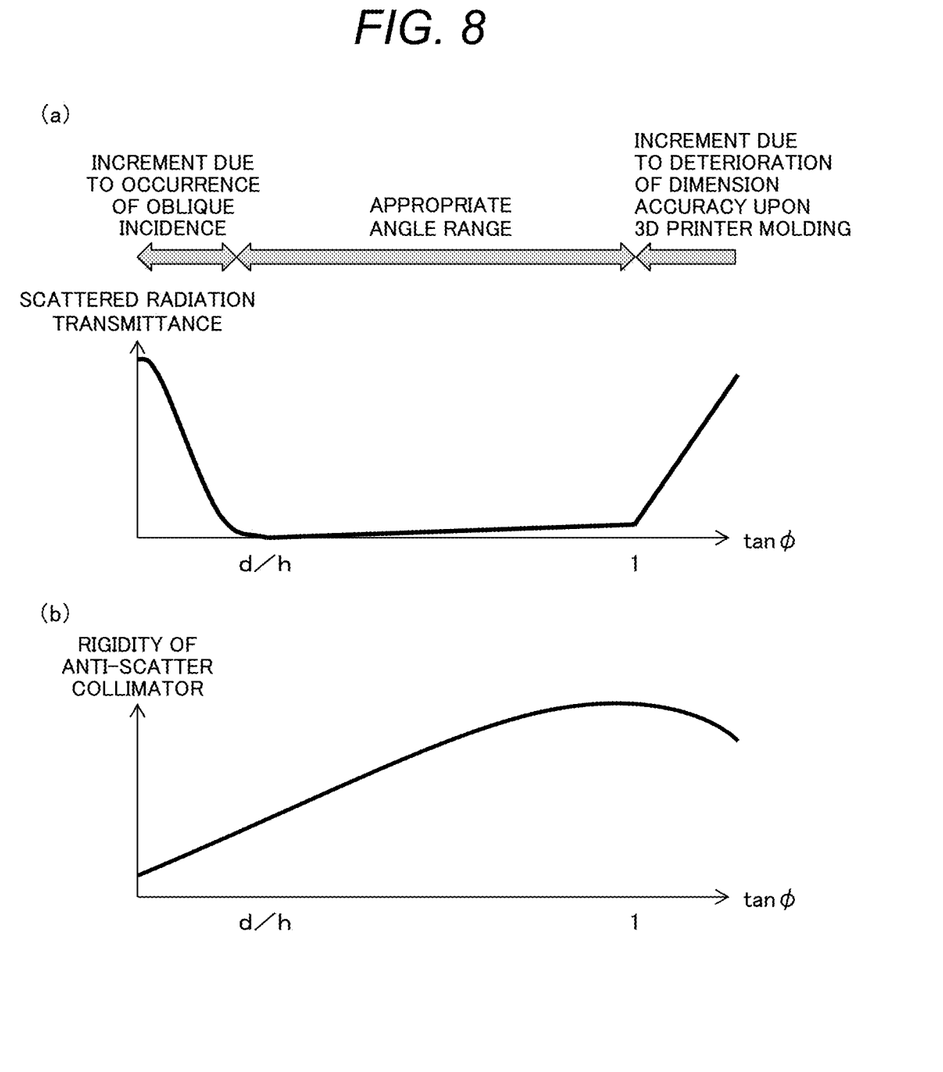
FIG. 8 is a diagram showing an appropriate range of an interior angle of a gap 203 according to the fourth embodiment.

Next, an appropriate range of the angle φ, i.e., the interior angle φ as an acute angle of the parallelogram, will be described by using FIG. 8. FIG. 8(a) shows the relationship between the angle φ and the scattered radiation shielding rate, and FIG. 8(b) shows the relationship between the angle φ and the rigidity of the anti-scatter collimator 108.

When the angle φ is too small, the gap 203 passes from the X-ray incident surface 200 to the surface of the semiconductor layer 109, and scattered radiation is transmitted to the adjacent pixels. To prevent transmission of scattered radiation to the adjacent pixels, as the lower value φL of the angle φ, tanφL=d/h holds. Further, to satisfy the necessary dimension accuracy in 3D printer molding, it is necessary that the angle φ is equal to or smaller than 45 degrees. The appropriate range of the angle φ, determined from the viewpoint of the scattered radiation shielding rate is represented with an (Expression 6).

$$d/h < \tan\phi \leq 1 \quad \text{(Expression 6)}$$

The rigidity of the anti-scatter collimator 108 is the maximum when tanφ=45 degrees holds, i.e., tanφ=1 holds. The rigidity is lowered in accordance with shift of the angle φ from 45 degrees. Accordingly, tanφ=1 is the best from the viewpoints of the scattered radiation shielding rate and the rigidity of the anti-scatter collimator 108. At least it is desirable to satisfy the (Expression 6).

Fifth Embodiment

In the fourth embodiment, it has been described that the shape of the gap 203 is a parallelogram, and the septum 202 is provided at an equal pitch in the X-ray incident direction (Y). In the present embodiment, as in the case of the second embodiment, the arrangement of the septum 202 in which the pitch in the X-ray incident direction (Y) is changed in the middle will be described. Note that the upper end of the top septum is made to correspond with the X-ray incident surface 200 as in the case of the first embodiment.

Figure 9:
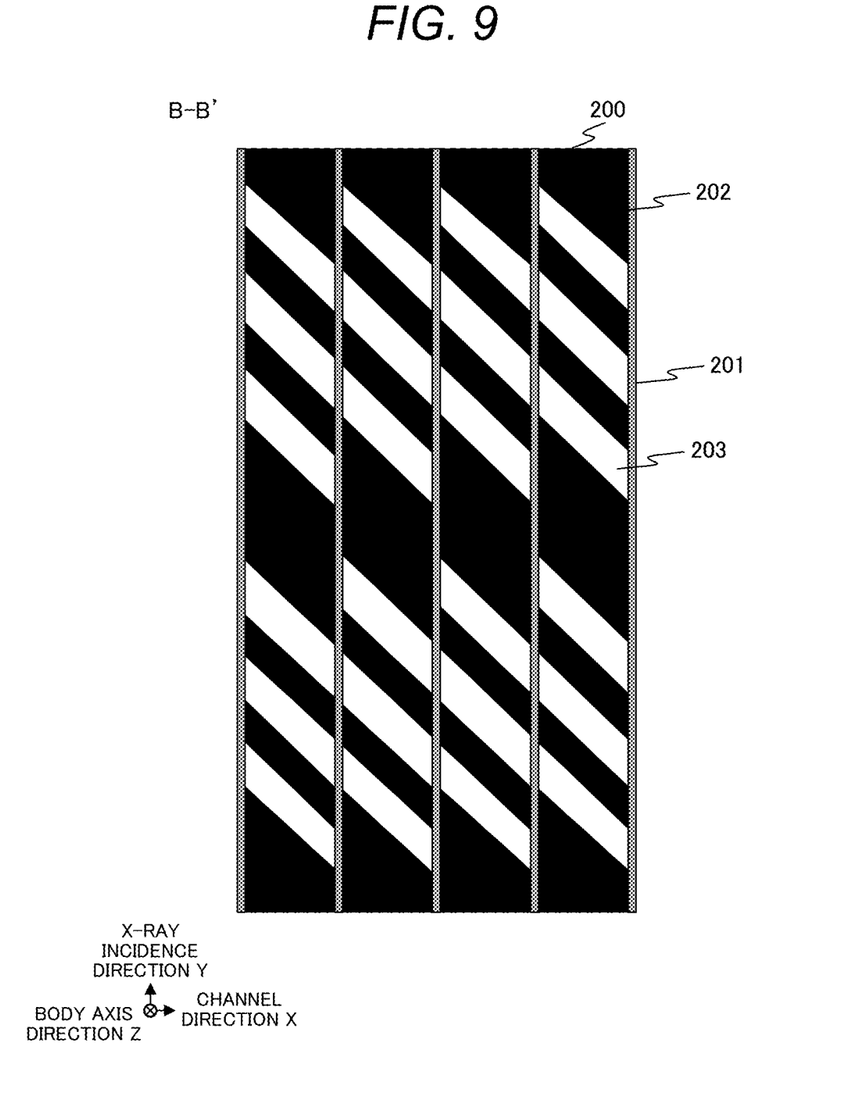
FIG. 9 is a diagram showing an example of the shape of the anti-scatter collimator according to a fifth embodiment.

The anti-scatter collimator 108 according to the present embodiment will be described by using FIG. 9. In FIG. 9, the septum 202 is provided at an equal pitch in the channel direction (X). In the X-ray incident direction (Y), the septum 202 is provided such that the position of the septum 202 is shifted by a half pitch in the intermediate position of the anti-scatter collimator 108. By changing the pitch in the intermediate position of the anti-scatter collimator 108, scattered radiation transmitted between the septa 202 in the upper half of the anti-scatter collimator 108 is shielded with the septum 202 in the lower half of the anti-scatter collimator 108. That is, as in the case of the second embodiment, it is possible to improve the scattered radiation shielding rate and to enhance the rigidity of the anti-scatter collimator 108.

Sixth Embodiment

In the fourth embodiment and the fifth embodiment, it has been described that the shape of the gap 203 is a parallelogram, and the shape is the same between adjacent pixels. In the present embodiment, the direction of the gap 203 is changed between adjacent pixels. Note that the upper end of the top septum is made to correspond with the X-ray incident surface 200 as in the case of the first embodiment.

Figure 10:
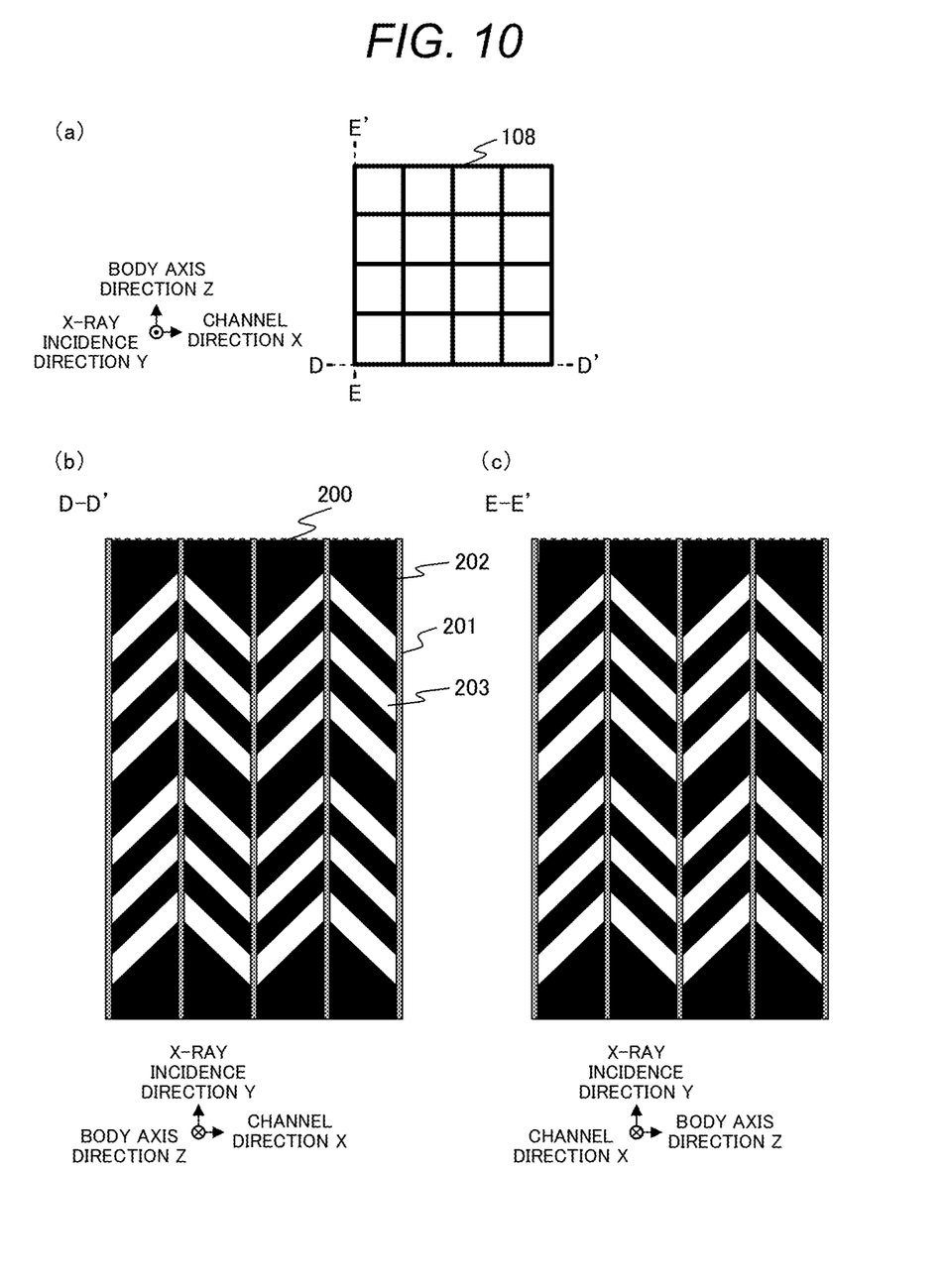
FIG. 10 is a diagram showing an example of the shape of the anti-scatter collimator according to a sixth embodiment.

The anti-scatter collimator 108 according to the present embodiment will be described by using FIG. 10. FIG. 10(a) is a plane view of the anti-scatter collimator 108, FIG. 10(b) is a D-D' cross-sectional view, and FIG. 10(c) is an E-E' cross-sectional view. The anti-scatter collimator 108 according to the present embodiment is different from the fourth embodiment in that the direction of the gap 203 is the opposite direction between adjacent pixels, and the parallelogram is symmetrical between the adjacent pixels. As the parallelogram is symmetrical between the adjacent pixels, the rigidity of the anti-scatter collimator 108 is improved with respect to load from a different direction.

Seventh Embodiment

In the first embodiment to the sixth embodiment, it has been described that the pillar 201 has a uniform shape in the X-ray incident direction (Y). To improve the rigidity of the anti-scatter collimator 108, the shape of the pillar 201 is changed in the present embodiment. Note that the upper end of the top septum is made to correspond with the X-ray incident surface 200 as in the case of the first embodiment.

Figure 11:
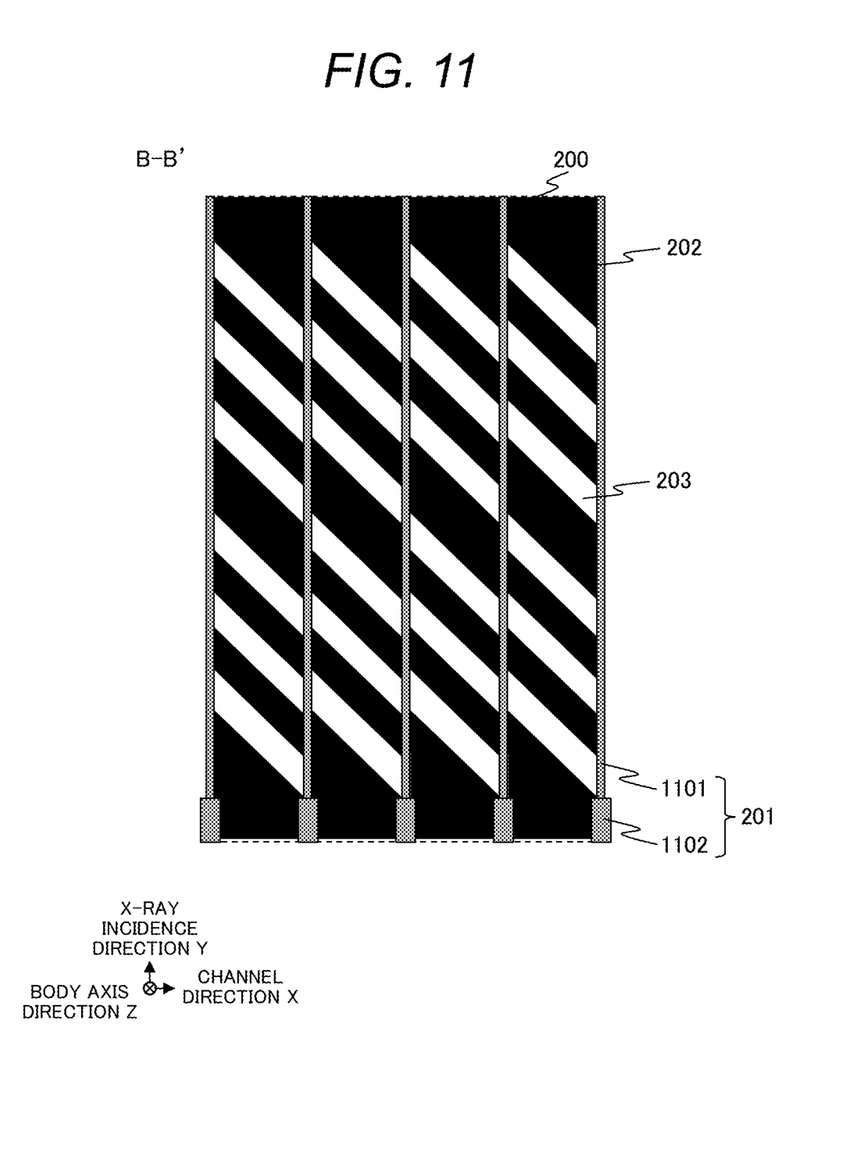
FIG. 11 is a diagram showing an example of the shape of the anti-scatter collimator according to a seventh embodiment.

The anti-scatter collimator 108 according to the present embodiment will be described by using FIG. 11. The pillar 201 according to the present embodiment has a stem 1101 and a base 1102. The base 1102 is provided on the semiconductor layer 109 side. The width of the base 1102 is wider than the width of the stem 1101. The cross-sectional shape of the pillar 201 along the X-ray incident direction (Y) is an inverted T shape. As the pillar 201 has the shape as shown in FIG. 11, the rigidity of the anti-scatter collimator 108 can be improved.

Note that the radiation imaging device according to the present invention is not limited to the above-described embodiments, and the radiation imaging device where the constituent element is changed can be embodied within a range not departing from the subject matter of the invention. Further, the plural constituent elements disclosed in the above-described embodiments may be arbitrarily combined. Further, some constituent elements may be deleted from all the constituent elements shown in the above-described embodiments. For example, the pillar 201 according to the seventh embodiment may be applied to the first embodiment to the sixth embodiment.

REFERENCE SIGNS LIST

100: X-ray source, 101: X-ray detector, 102: signal processor, 103: image generator, 104: rotary table, 105: bed, 106: subject, 107: detection element module, 108:

anti-scatter collimator, 109: semiconductor layer, 110: scanner, 200: X-ray incident surface, 201: pillar, 202: septum, 202a: septum, 202b: septum, 202c: septum, 202d: septum, 203: gap, 204: pixel, 301: frame, 302: wire, 401: vertical line, 402: route, 403: route, 501: route, 1101: stem, and 1102: base.

The invention claimed is:

1. A radiation imaging device comprising: a radiation source;
   a radiation detector that detects radiation emitted from a focus of the radiation source; and an anti-scatter collimator provided between the radiation source and the radiation detector,
   wherein the anti-scatter collimator has a septum provided at a predetermined interval along a radiation incident direction on a boundary between pixels of the radiation detector, and an upper end of a top septum corresponds with the radiation incident surface,
   wherein the shape of a gap between the septa and pillars that support the septum is a parallelogram.

2. The radiation imaging device according to claim 1, wherein assuming that an interior angle of the parallelogram as an acute angle is $\phi$, the width between the septa is d, and the height of the anti-scatter collimator is h, $d/h < \tan\phi \leq 1$ holds.

3. The radiation imaging device according to claim 2, wherein $\tan\phi = 1$ holds.

4. The radiation imaging device according to claim 1, wherein the parallelogram has the same shape between adjacent pixels.

5. The radiation imaging device according to claim 1, wherein the parallelogram is symmetrical between the adjacent pixels.

6. A radiation imaging device comprising: a radiation source;
   a radiation detector that detects radiation emitted from a focus of the radiation source; and an anti-scatter collimator provided between the radiation source and the radiation detector,
   wherein the anti-scatter collimator has a septum provided at a predetermined interval along a radiation incident direction on a boundary between pixels of the radiation detector, and an upper end of a top septum corresponds with the radiation incident surface,
   wherein the septum is provided respectively at an equal pitch with respect to the radiation incident direction and an array direction of the pixels, and assuming that the height of the septum in the radiation incident direction is b, the thickness in the pixel array direction is t, the interval between the septa in the radiation incident direction is s, and the pixel array direction is d, $s < t \cdot b/d$ holds.

7. A radiation imaging device comprising: a radiation source;
   a radiation detector that detects radiation emitted from a focus of the radiation source; and an anti-scatter collimator provided between the radiation source and the radiation detector,
   wherein the anti-scatter collimator has a septum provided at a predetermined interval along a radiation incident direction on a boundary between pixels of the radiation detector, and an upper end of a top septum corresponds with the radiation incident surface,
   wherein the anti-scatter collimator is divided into N in the radiation incident direction, and the position of the septum is shifted by 1/N pitch and the septum is provided in each dividing position.

8. A radiation imaging device comprising: a radiation source;
   a radiation detector that detects radiation emitted from a focus of the radiation source; and an anti-scatter collimator provided between the radiation source and the radiation detector,
   wherein the anti-scatter collimator has a septum provided at a predetermined interval along a radiation incident direction on a boundary between pixels of the radiation detector, and an upper end of a top septum corresponds with the radiation incident surface,
   wherein the width of the gap between the septa is wider on the side closer to the radiation source.

9. A radiation imaging device comprising: a radiation source;
   a radiation detector that detects radiation emitted from a focus of the radiation source; and an anti-scatter collimator provided between the radiation source and the radiation detector,
   wherein the anti-scatter collimator has a septum provided at a predetermined interval along a radiation incident direction on a boundary between pixels of the radiation detector, and an upper end of a top septum corresponds with the radiation incident surface,
   wherein the septum is provided at an equal pitch with respect to the pixel array direction, and assuming that the height of the septum in the radiation incident direction is b, the thickness in the pixel array direction is t, a position in the radiation incident direction is y, the interval between the septa in the radiation incident direction is s(y), the pixel array direction is d, and the height of the anti-scatter collimator in the radiation incident direction is h, $s(y)=b$ $(y \leq h/2)$, $t \cdot y/d (y > h/2)$ or $s(y)=b$ $(y \leq b \cdot d/t)$, $t \cdot y/d (y > b \cdot d/t)$ hold.

10. A radiation imaging device comprising: a radiation source;
    a radiation detector that detects radiation emitted from a focus of the radiation source; and an anti-scatter collimator provided between the radiation source and the radiation detector,
    wherein the anti-scatter collimator has a septum provided at a predetermined interval along a radiation incident direction on a boundary between pixels of the radiation detector, and an upper end of a top septum corresponds with the radiation incident surface,
    wherein among the septa provided along the radiation incident direction, the height of the septum provided in an intermediate position of the anti-scatter collimator is higher in comparison with other septa.

11. A radiation imaging device comprising: a radiation source;
    a radiation detector that detects radiation emitted from a focus of the radiation source; and an anti-scatter collimator provided between the radiation source and the radiation detector,
    wherein the anti-scatter collimator has a septum provided at a predetermined interval along a radiation incident direction on a boundary between pixels of the radiation detector, and an upper end of a top septum corresponds with the radiation incident surface,
    wherein a pillar that supports the septum is provided immediately above the four corners of the pixel of the radiation detector, and has a base on the side of the radiation detector,
    wherein the width of the base is wider than the width of the others.

* * * * *